US00PP17587P3

(12) United States Plant Patent
Pulling, Jr.

(10) Patent No.: US PP17,587 P3
(45) Date of Patent: Apr. 10, 2007

(54) *EUPHORBIA MILII* PLANT NAMED 'KATIE'S CROWN'

(50) Latin Name: *Euphorbia milii*
Varietal Denomination: Katie's Crown

(76) Inventor: John A. Pulling, Jr., 6500 Airport Pulling Rd. N., Naples, FL (US) 34109

( * ) Notice: Subject to any disclaimer, the term of this patent is extended or adjusted under 35 U.S.C. 154(b) by 10 days.

(21) Appl. No.: 11/120,895

(22) Filed: May 3, 2005

(65) Prior Publication Data

US 2006/0253948 P1 Nov. 9, 2006

(51) Int. Cl.
*A01H 5/00* (2006.01)

(52) U.S. Cl. ..... Plt./302
(58) Field of Classification Search ..... Plt./302
See application file for complete search history.

(56) References Cited

U.S. PATENT DOCUMENTS

| | | | |
|---|---|---|---|
| PP12,510 | P2 | 4/2002 | Yokoi |
| PP12,782 | P2 | 7/2002 | Fruehwirth |
| PP14,246 | P2 | 10/2003 | Lucas |
| PP14,280 | P2 | 11/2003 | Dummen |
| PP14,514 | P2 | 2/2004 | Heims |
| PP14,559 | P2 | 2/2004 | Drewlow |
| PP14,572 | P2 | 3/2004 | Heims |
| PP14,630 | P2 | 3/2004 | Voogt |
| PP14,868 | P2 | 6/2004 | White |

*Primary Examiner*—Kent Bell
*Assistant Examiner*—Louanne Krawczewicz Myers

(57) ABSTRACT

A new distinct cultivar of *Euphorbia milii* plant named 'Katie's Crown', particularly characterized by its hot pink floral bracts splotched with red color, gradually becoming lighter to an almost cream color splotched with red when aged; very compact and bushy plant form; non-persistent blooms; rigorous growth habit during the spring to autumn months and flowering during the fall, winter and spring.

16 Drawing Sheets

Genus and species of the plant claimed: *Euphorbia milii.* Variety domination: 'Katie's Crown'.

BACKGROUND OF THE INVENTION

The present invention relates to a new and distinct cultiver of *Euphorbia milii* plant, commonly known as Crown of Thorns, hereinafter referred to by the name 'Katie's Crown'.

The new *Euphorbia milii* is the product of a natural breeding program conducted by the inventor, John A Pulling Jr. in Naples, Fla. The new *Euphorbia milii* originated from a polycross made in the year 2003 in the inventor's garden in Naples. The parental cultivars are unnamed and nonpatented seedlings of *Euphorbia milii.* Seeds were collected from several varieties of *Euphorbia milii* in the inventor's backyard. The seeds were planted in community pots and let sprout and grow. As the seedlings grew, they were planted in six inch pots and grown for a year. The new *Euphorbia milii* cultivar was chosen from about three hundred seedlings propagated in the year 2003. The new plant was selected based upon its rapid compact growth, flower color, nonpersistent blooms, freely branching habit and high resistance to insects and disease. The plants are bushy, compact and have an abundance of mottled hot pink flowers which cover the plant during the flowering period.

Asexual reproduction of the new cultivar by cuttings harvested and propagated in trial production batches at Naples, Fla. have shown that the unique features of this new *Euphorbia milii* are stable and reproducible true to type in successive generations of asexual reproduction. In the spring of 2004, about 15 cuttings were taken from the new plant and a second and third generation of cuttings have been taken from these offspring. All plants have reproduced true to type.

The new *Euphorbia milii* had cuttings taken from it in March of 2004. The cuttings were planted in potting soil in four inch pots, then placed outdoors under partial shade and watered once a day by hand. Initial rooting in the four inch pots started in about three weeks. After being well rooted, they were transferred to six inch pots for a period of time and then finally transferred to eight inch pots. From the initial cuttings planted in March 2004, the plants grew to a height of about 30 cm by October 2004. The plants were fertilized during the growing period with dry granular fertilizer at two month intervals.

BRIEF DESCRIPTION OF DIFFERENCES

Plants of the new cultivar 'Katie's Crown' can be compared to the unidentified plant in the inventors garden that looks most similar to it, by the following side by side comparisons: The cultivar that looks most similar to 'Katie's Crown' was part of a group of plants purchased from Thailand several years ago and for identification purposes in this description, hereinafter referred to as "Thai 1". 'Thai 1' is very similar in outward appearance to 'Katie's Crown', except for the following characteristics. 'Thai 1' has a much darker red background (46 D) and much darker red splotches (46 A) on its cyathophylls than 'Katie's Crown' which is more of a light red color (50 C) with dark red splotches (53 B). The glands of 'Thai 1' are an orange red (N 30 B) color compared to a yellow orange (14 A) on 'Katie's Crown'. The leaves on 'Thai 1', while having almost the same shape and color as 'Katie's Crown', are slightly larger at 10 cm length and 4 cm wide, while the leaves on 'Katie's Crown' are 8.3 cm in length and 3 cm wide. The Peduncles on 'Thai 1' are somewhat shorter at 4 cm in length, but much thicker at 4.5 mm in width than 'Katie's Crown'. Color of the peduncles on 'Thai 1' are much darker (183 B) as opposed to the grayed orange (173 A) of 'Katie's Crown'. The biggest difference in the two *Euphorbias* is in their flowering and growth. 'Thai 1' produces beautiful color bracts all year round and does not stop blooming in the summer. This characteristic may sound good, but because this plant blooms all the time, its growth rate is exceedingly slow. A plant that would take 3 months to grow of 'Katie's Crown' would be over a year old of 'Thai 1' with the same care. The second major difference between the two cultivars is that 'Thai 1' is not at all free branching, stems that are tip cut on 'Thai 1' finish blooming and slowing lose their leaves without branching. Sometimes one or two new stems will appear at the very bottom of a stem, but the major portion of the stem does not branch. 'Katie's Crown' is very free branching, if a tip is cut, new stems will form all up and down the remaining part of the stem. This allows the plant to be trimmed and yet still maintain its height and bushy appearance.

BRIEF DESCRIPTION OF THE INVENTION

Plants of the cultivar 'Katie's Crown' have not been observed under all possible environmental conditions. The phenotype may vary somewhat with variations in environment, such as temperature, light intensity, day length and fertility level without, however, any variance in genotype.

The following traits have been repeatedly observed and are determined to be unique characteristics of 'Katie's Crown'. These characteristics in combination distinguish 'Katie's Crown' as a new and distinct cultivar:

1. Hot pink floral bracts splotched with red, and with age gradually become lighter and lighter to almost a cream color splotched with red.
2. Very compact and bushy plant form, with multiple offshoots coming from each stem.
3. Very vigorous growth habit during the spring through autumn and flowering during the fall, winter and spring. As flowering commences in the fall, the growth rate slows dramatically, then resumes the following spring.
4. Flowers mostly in multiples of two or four on slender green peduncles.
5. Multiple flower shoots coming from a single stem, often as many as nine or ten. The plants start blooming in South Florida around October 1st and bloom all winter. Blooming ends in late spring or early summer.
6. The new cultivar holds leaves down the stem at least 20 cm, which adds to its bushy appearance.
7. The new free branching cultivar readily sends off offshoots, where a fallen leaf had been attached, new branches will form.
8. Although 'Katie's Crown' may be rooted at any time of the year, cuttings taken during the winter months are slow to grow. They will root within a short period of time, but as soon as the colder winter season approaches in South Florida, the plant puts its entire energy into blooming with no further growth taking place. For this reason, it is preferred to take cuttings in the spring, when the plant is in its growth period, as opposed to its bloom period.

BRIEF DESCRIPTION OF THE PHOTOGRAPHS

The accompanying color photographs illustrate the overall appearance and details of inflorescence form, color and structure of the new cultivar, showing colors as accurately as true as it is reasonably possible to obtain in colored reproductions of this type. Colors in the photographs may vary slightly from the color values cited in the detailed botanical description, which more accurately describes the actual colors of the *Euphorbia milii.*

Figure 1:
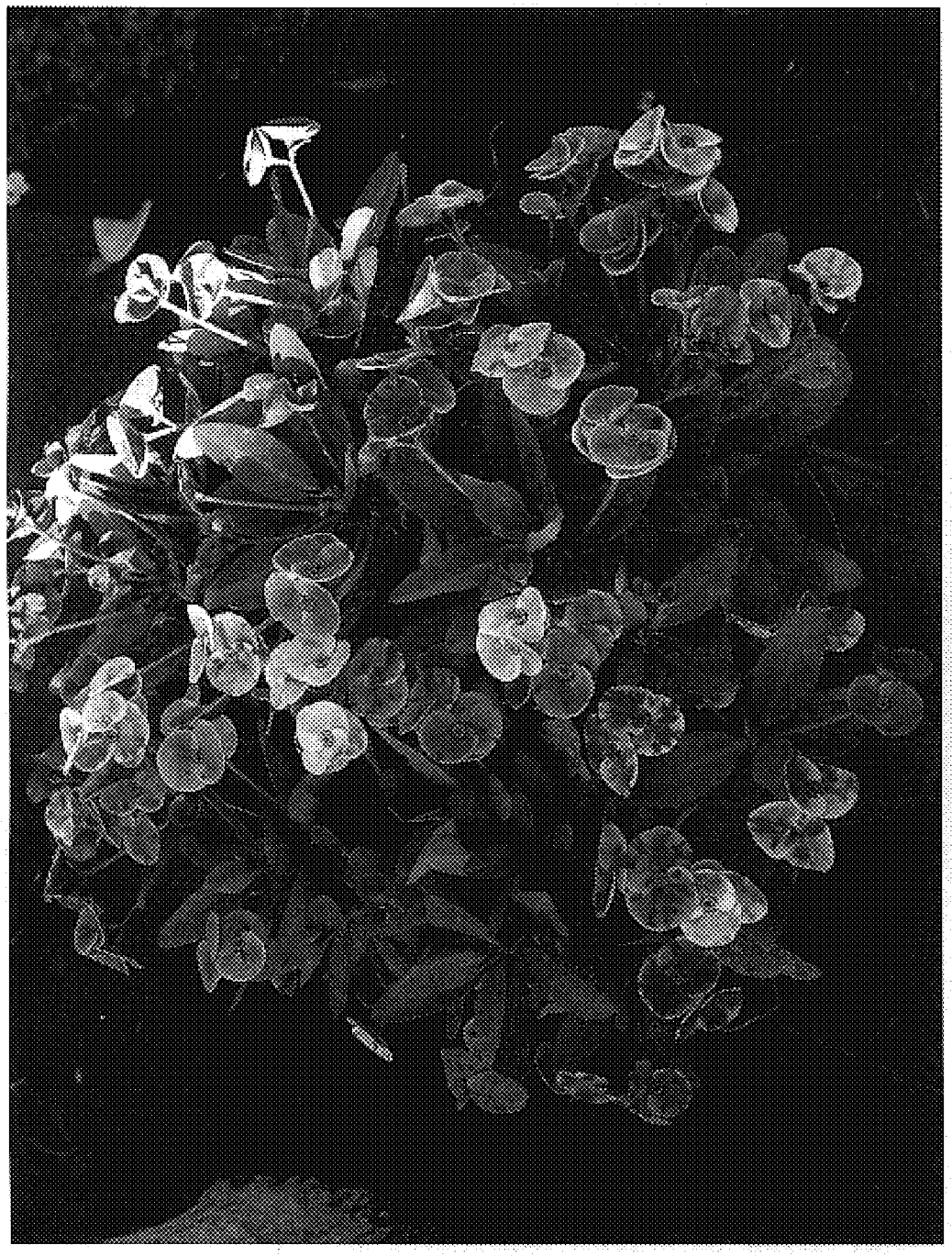
FIG. 1 shows a front view of 'Katie's Crown' as a finished flowering plant, about eight months old in an eight inch pot. This plant is about 30 cm high from the soil and about 30 cm wide.
Figure 2:
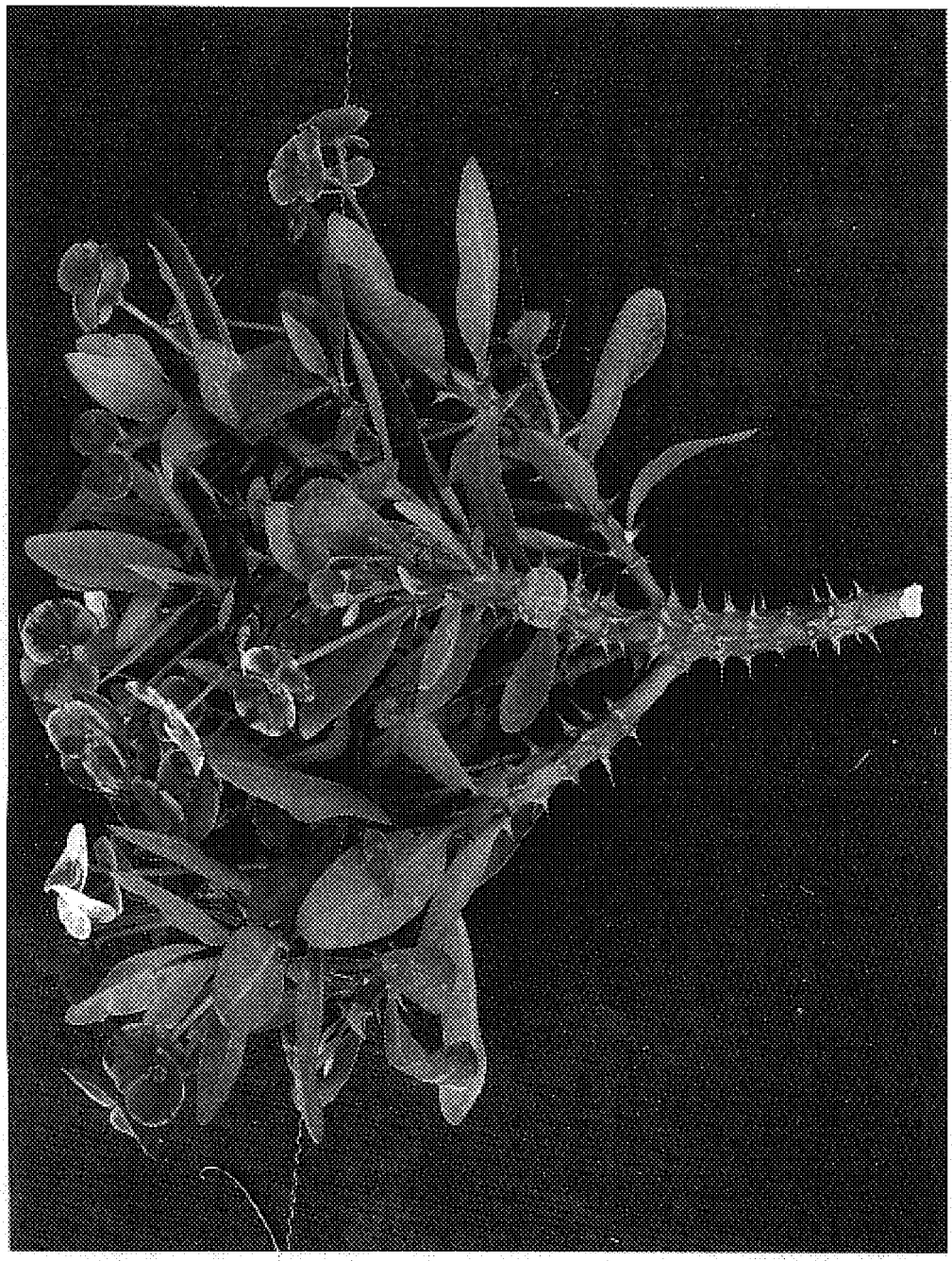
FIG. 2 shows a typical offshoot of a flowering plant showing its branching habit.
Figure 3:
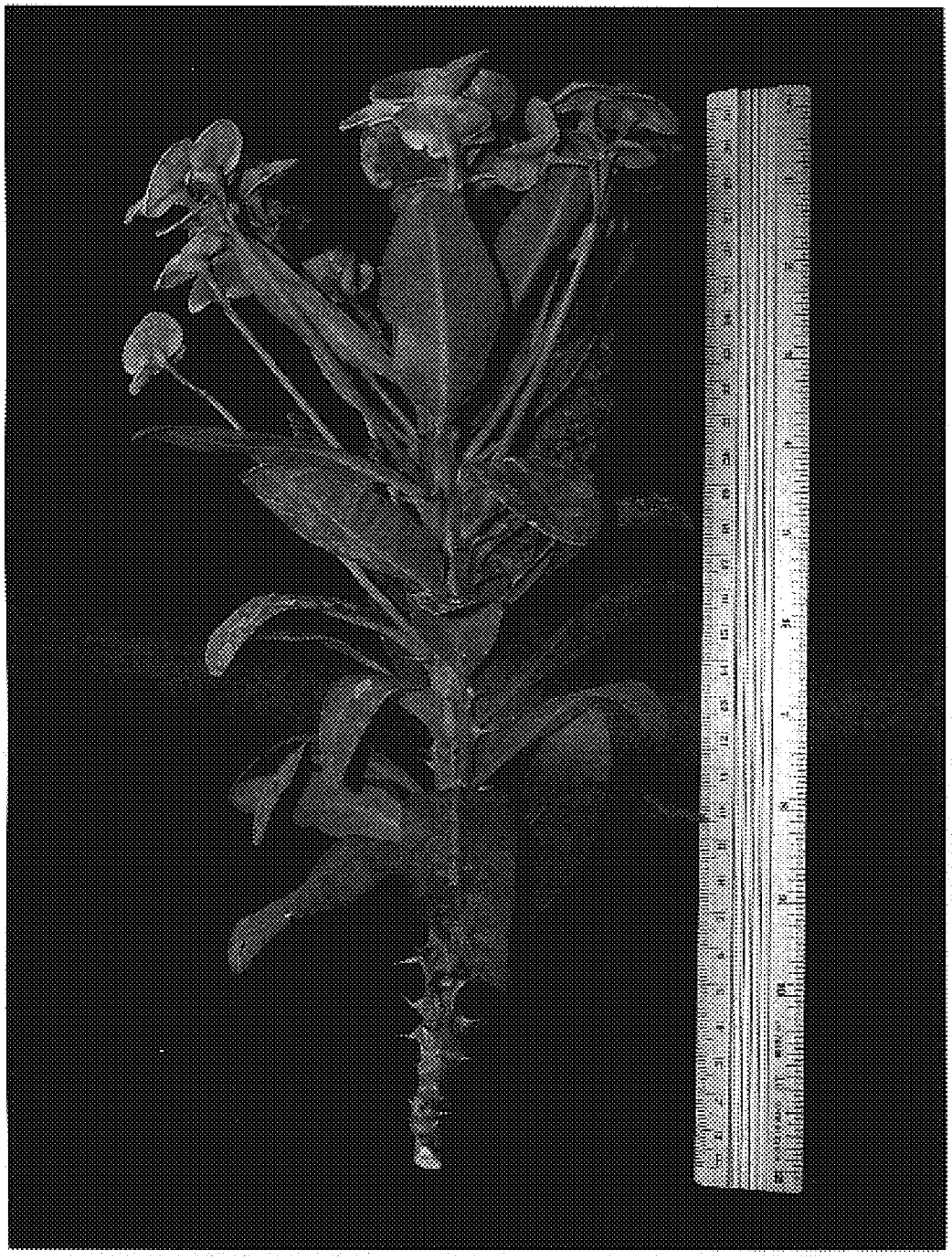
FIG. 3 shows a typical interior branch of a flowering plant showing 30 cm length of stem, downward growth of leaves on stem and blooming habit of typical stem.
Figure 4:
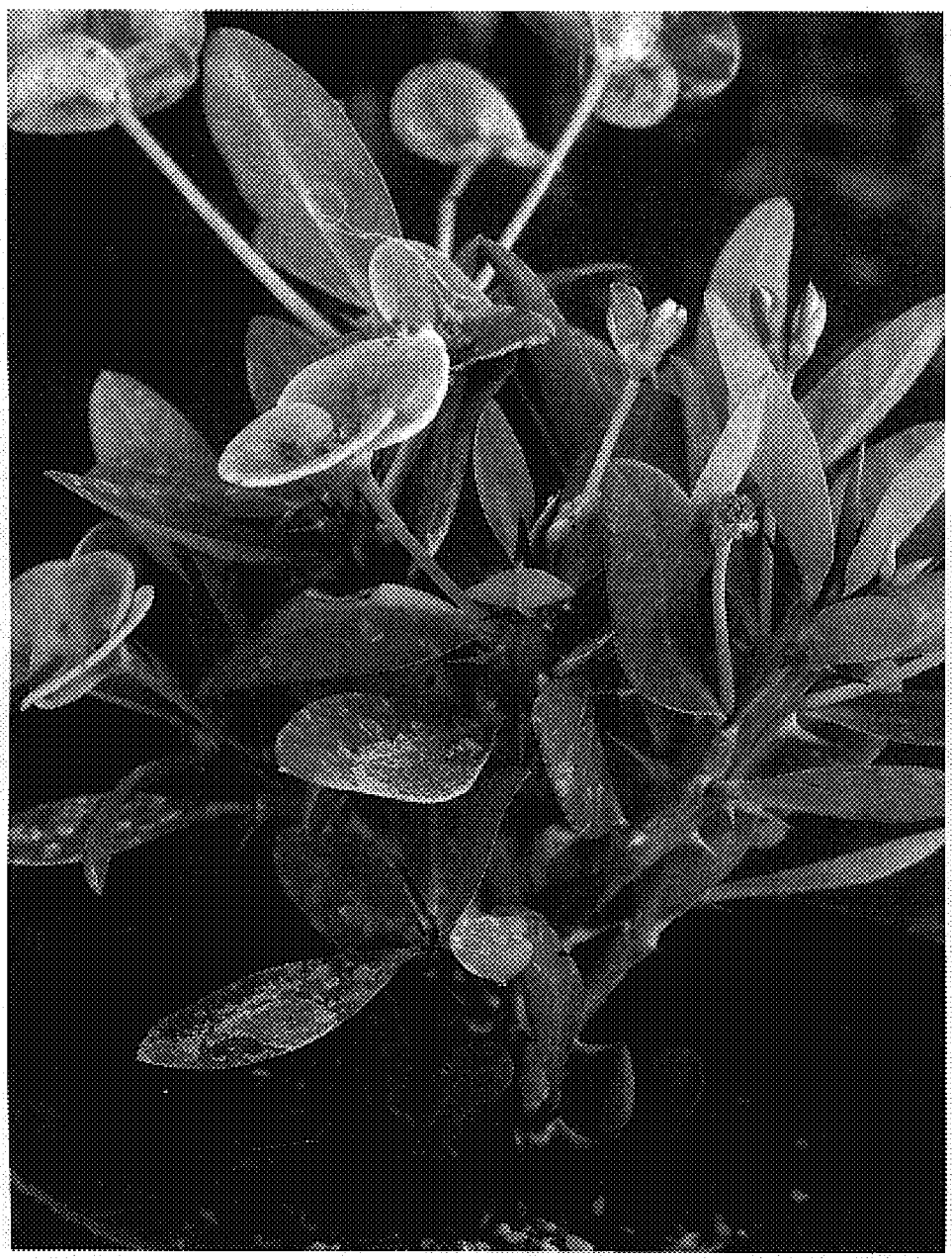
FIG. 4 shows typical 3 month old cutting showing its branching ability.
Figure 5:
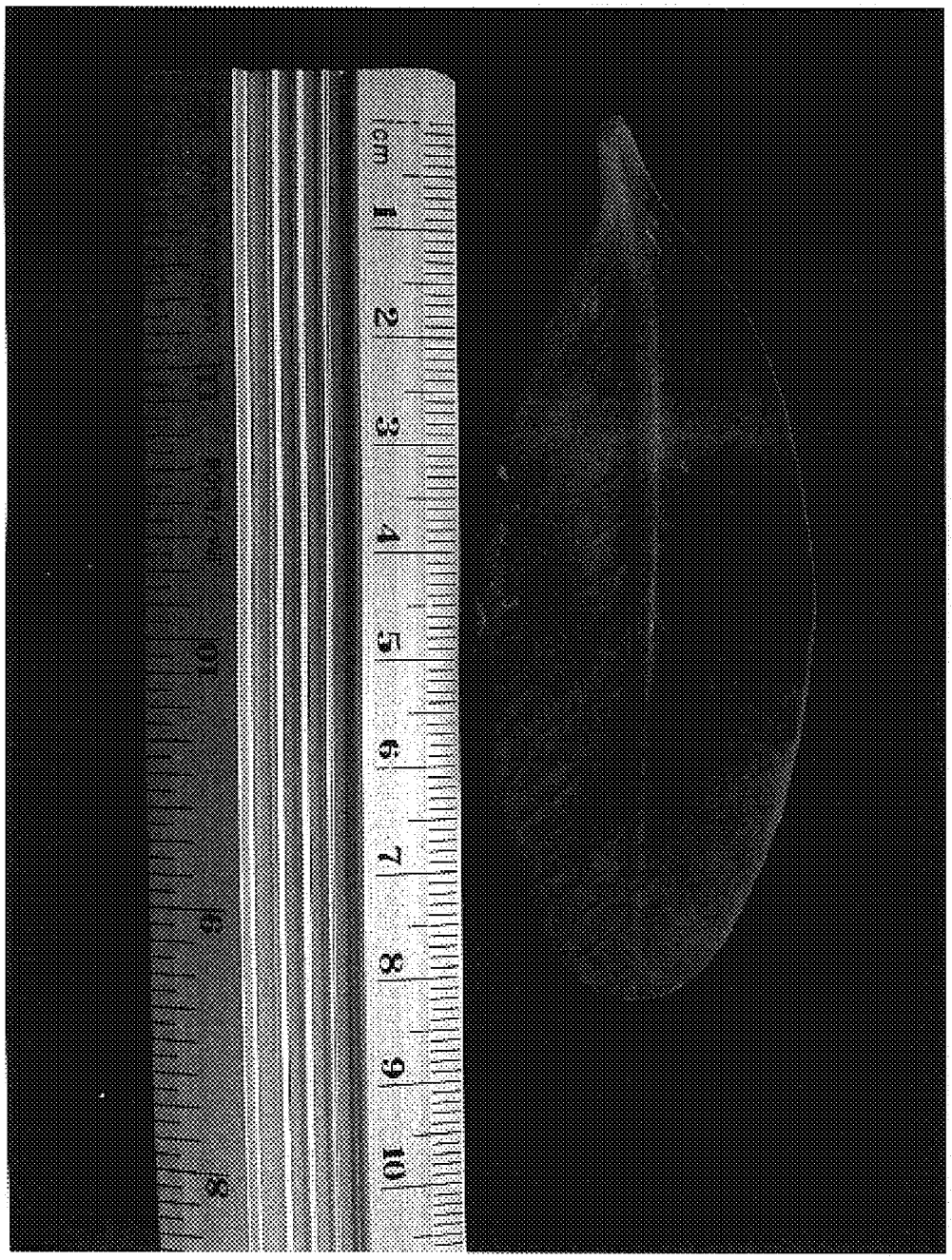
FIG. 5 shows an average length of a mature leaf, about 8.3 cm.
Figure 6:
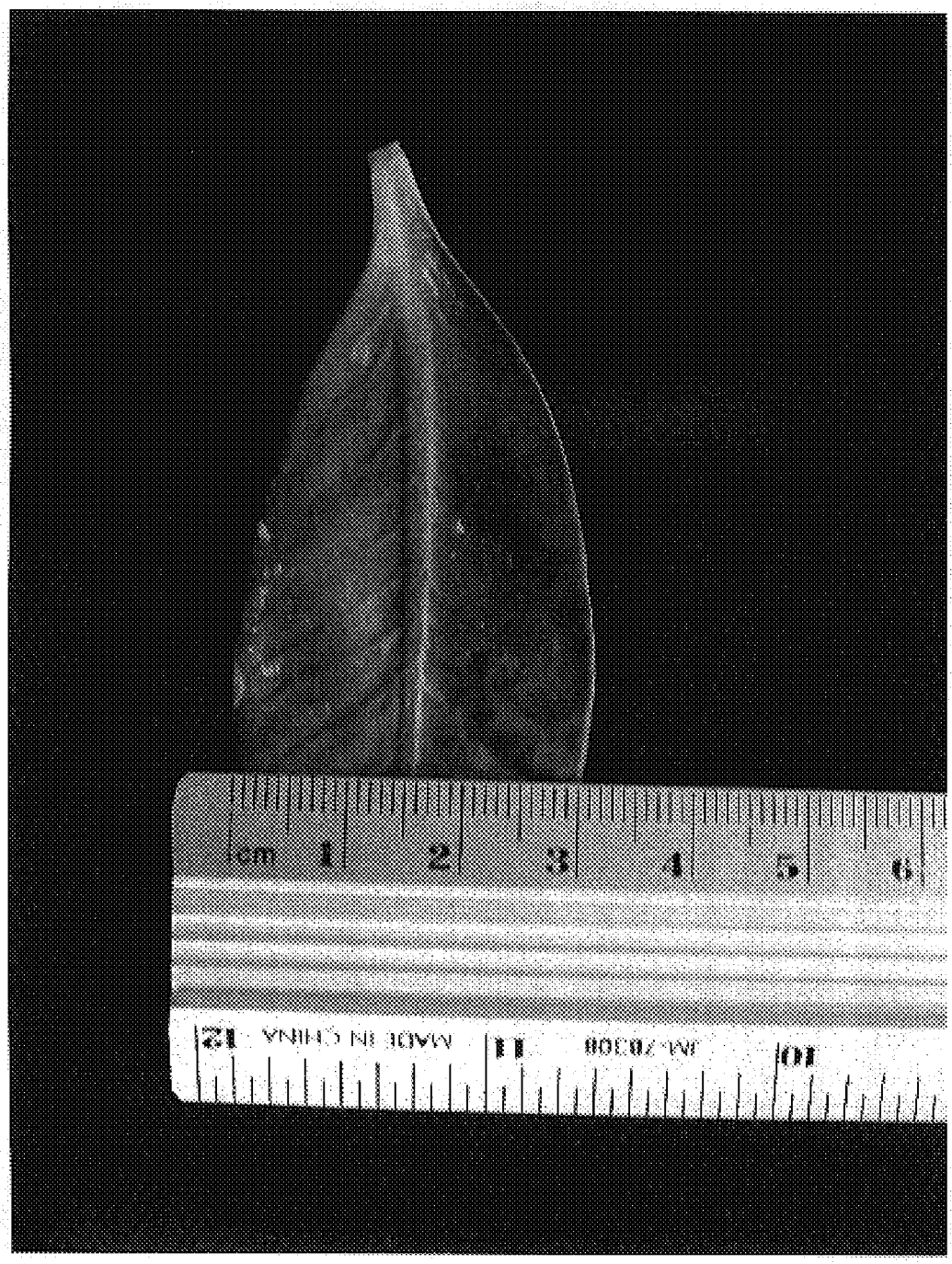
FIG. 6 shows an average width of a mature leaf, about 3 cm.
Figure 7:
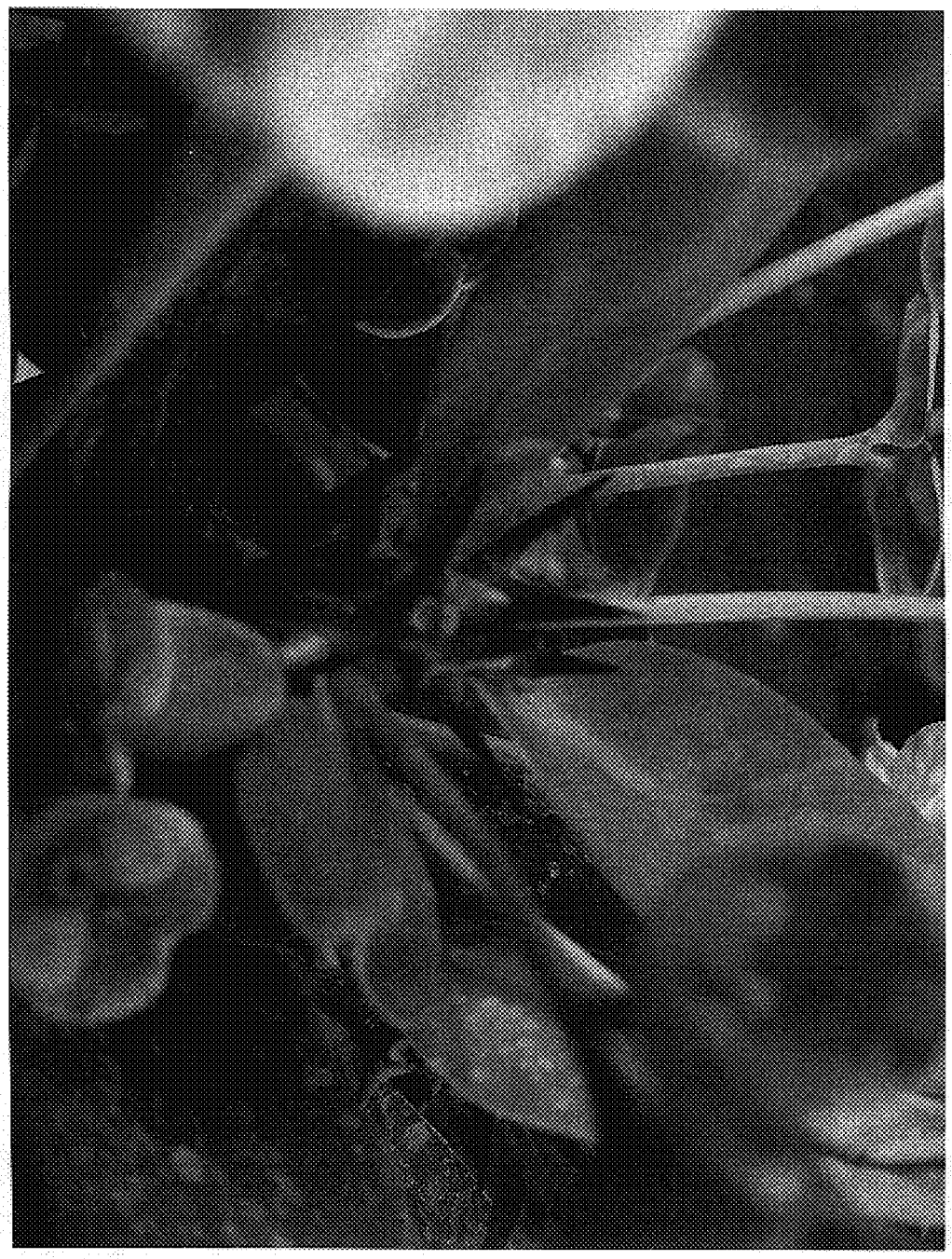
FIG. 7 shows bright color of new thorns as they emerge from the stem.
Figure 8:
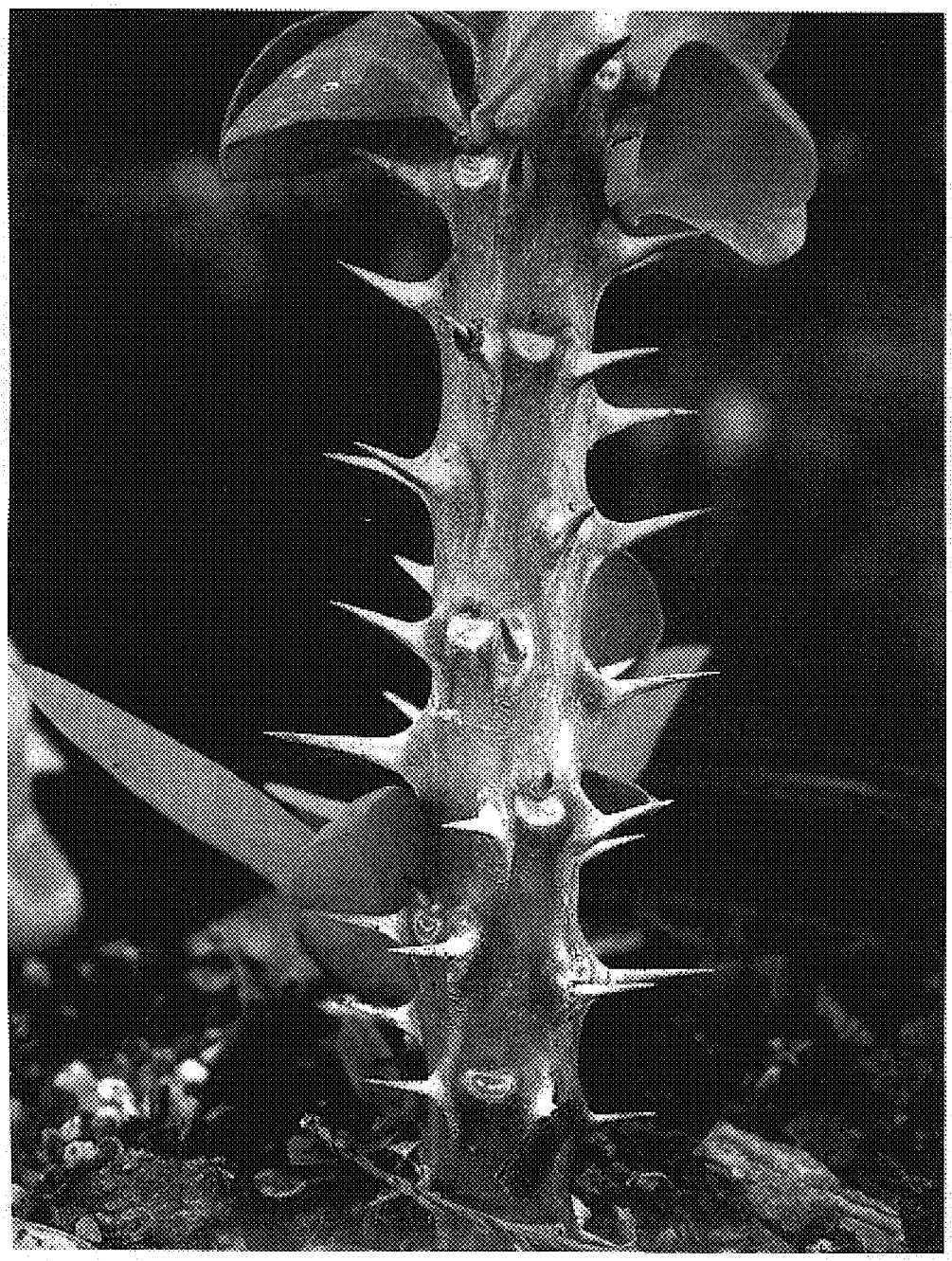
FIG. 8 shows a close-up view of the branching ability of new cuttings. A new branch forms where an old leaf was attached.
Figure 9:
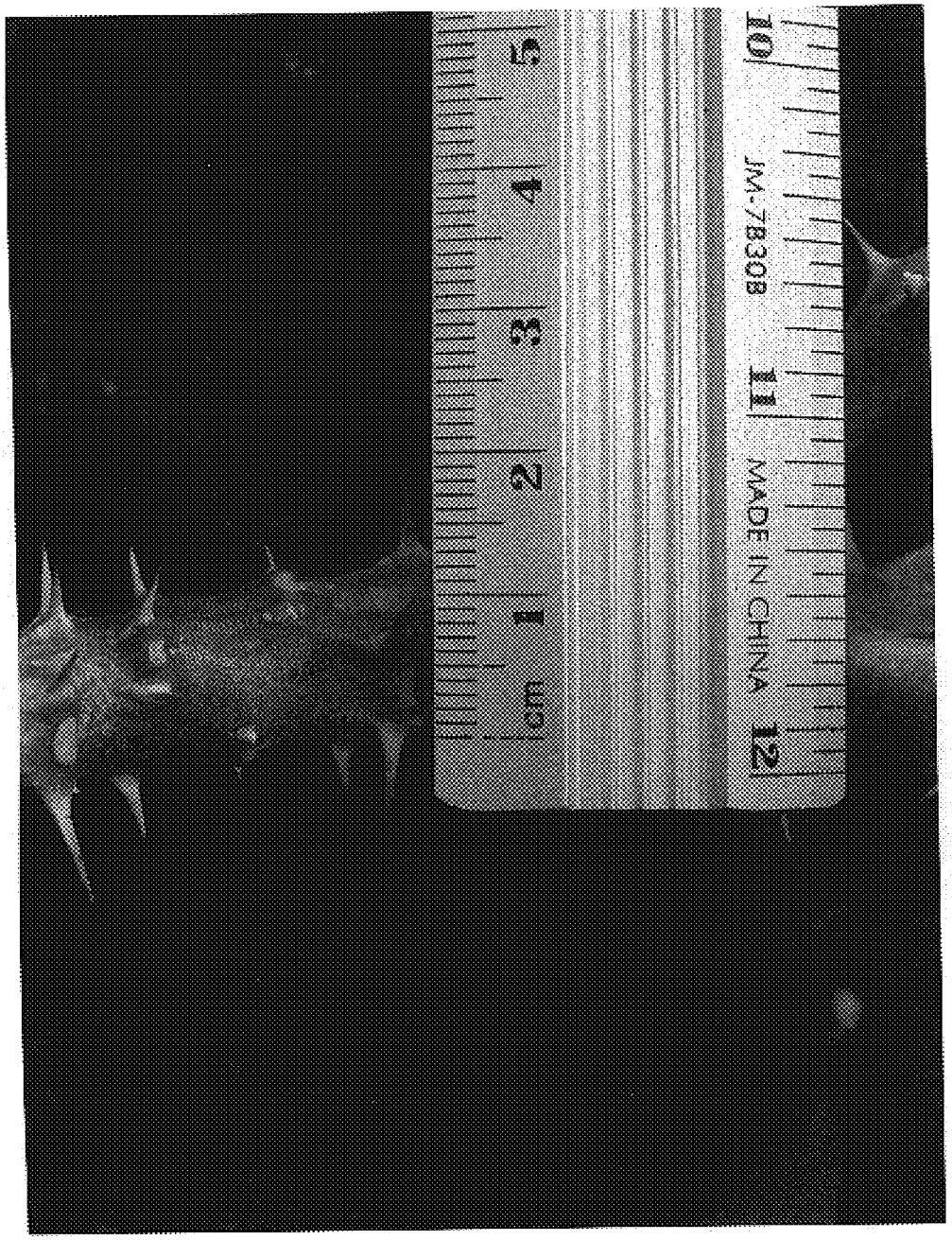
FIG. 9 shows the average width of an eight month old stem, about 1.3 cm across.
Figure 10:
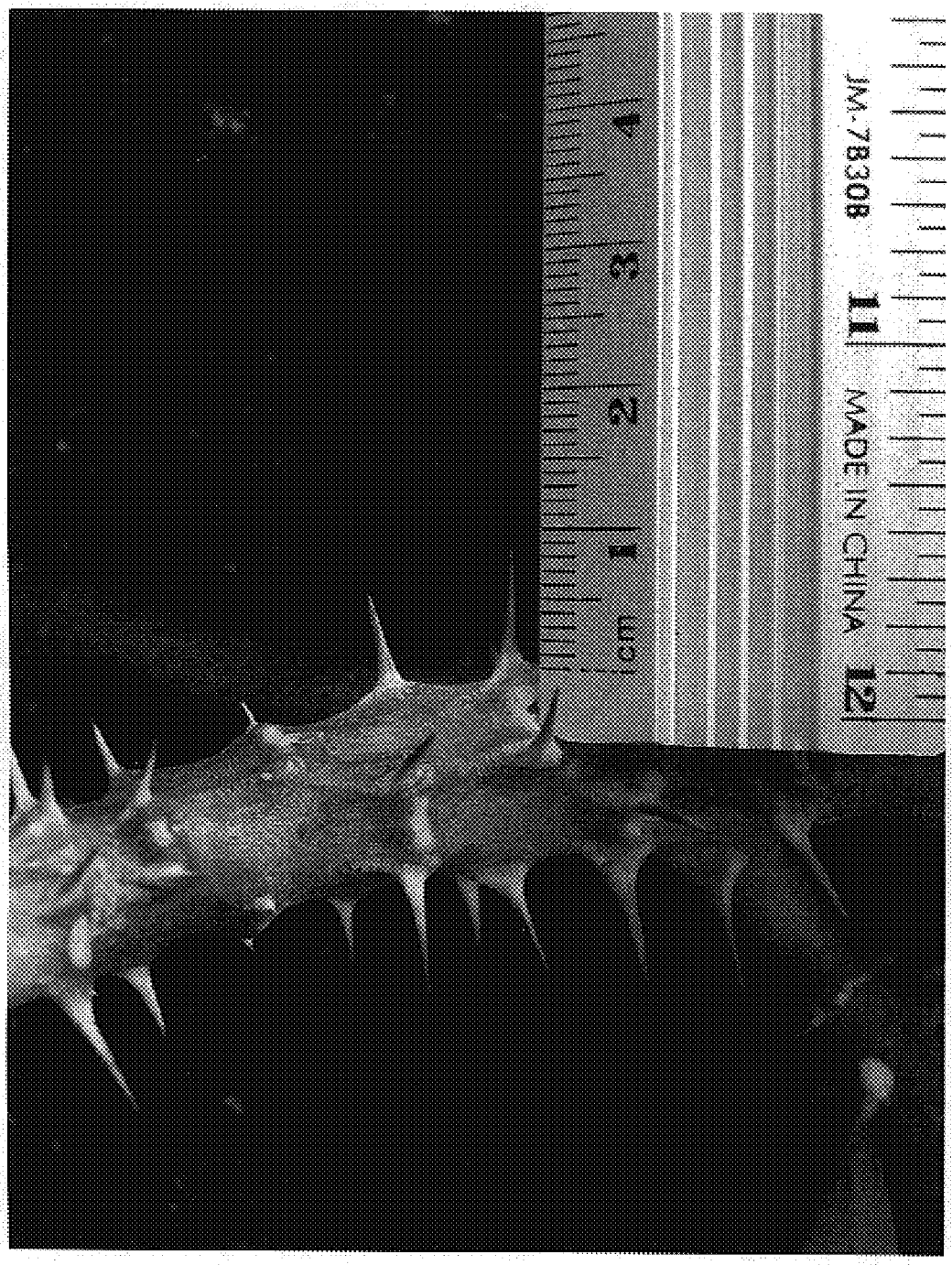
FIG. 10 shows the average length of a mature thorn, about 9 cm.
Figure 11:
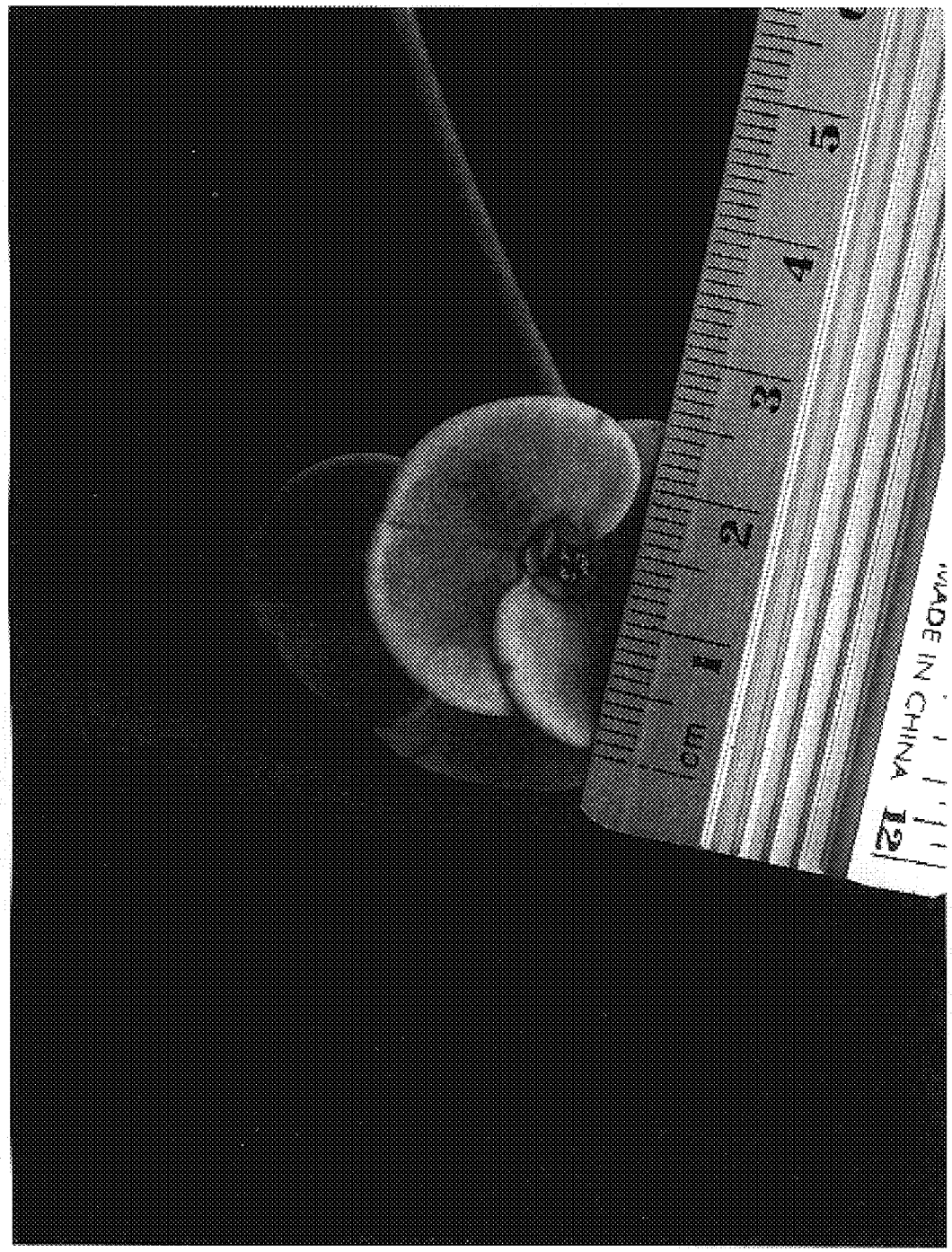
FIG. 11 shows the length of the large colorful bracts called cyathophylls*, about 2.5 cm.
Figure 12:
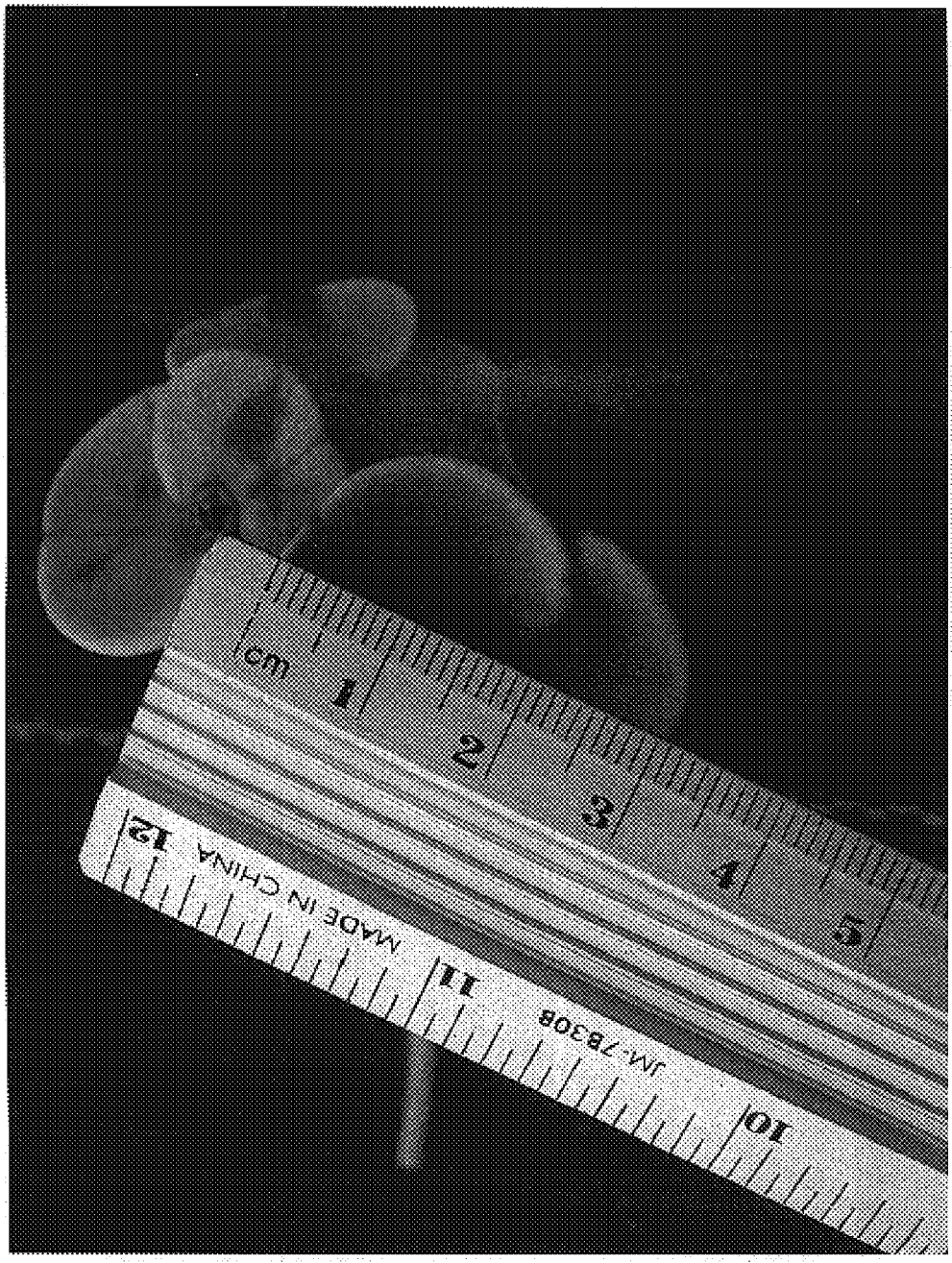
FIG. 12 shows width of cyathophylls*, about 3 cm.
Figure 13:
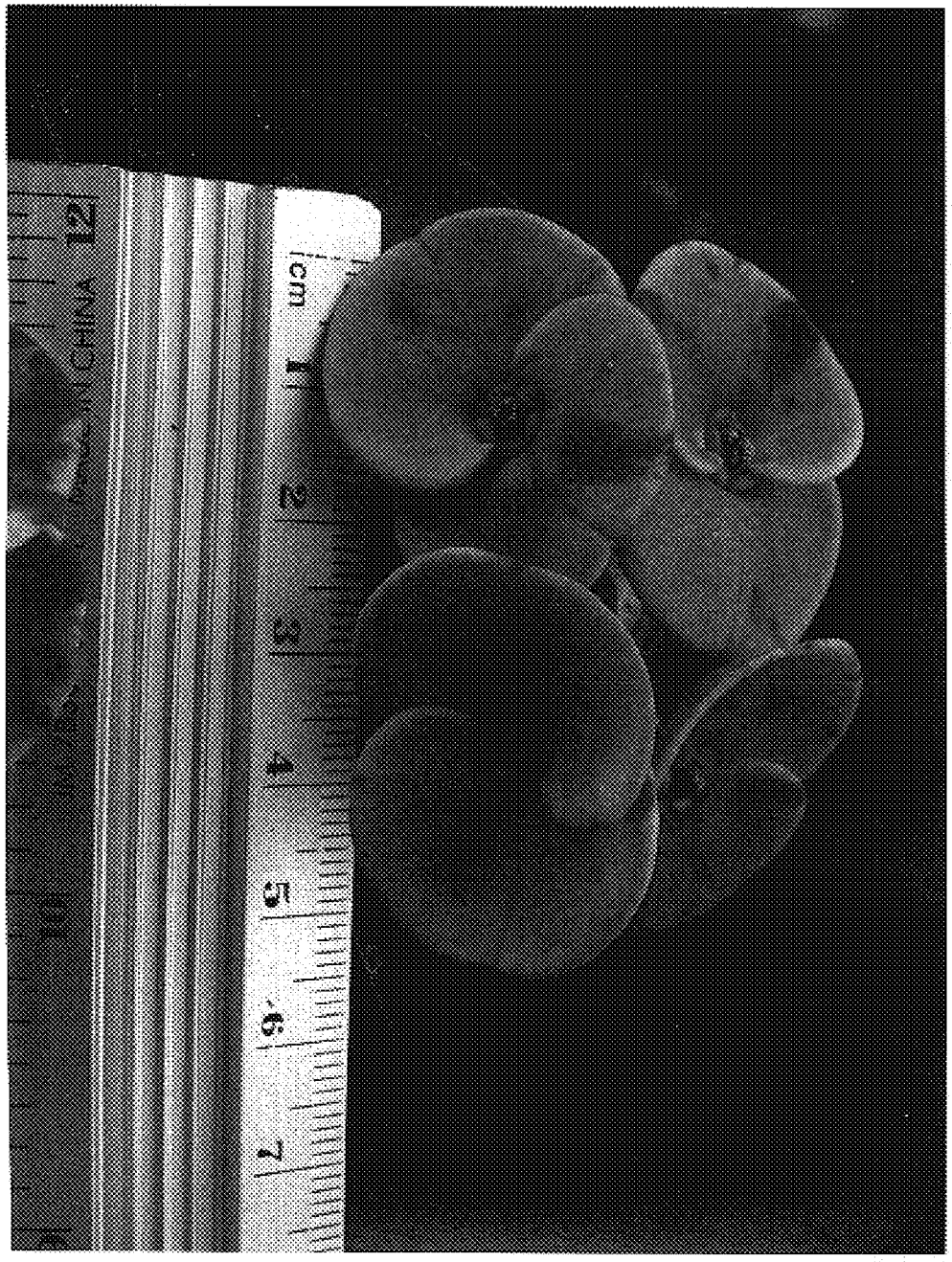
FIG. 13 shows the length of a typical inflorescence consisting of four cyathia, about 6 cm.
Figure 14:
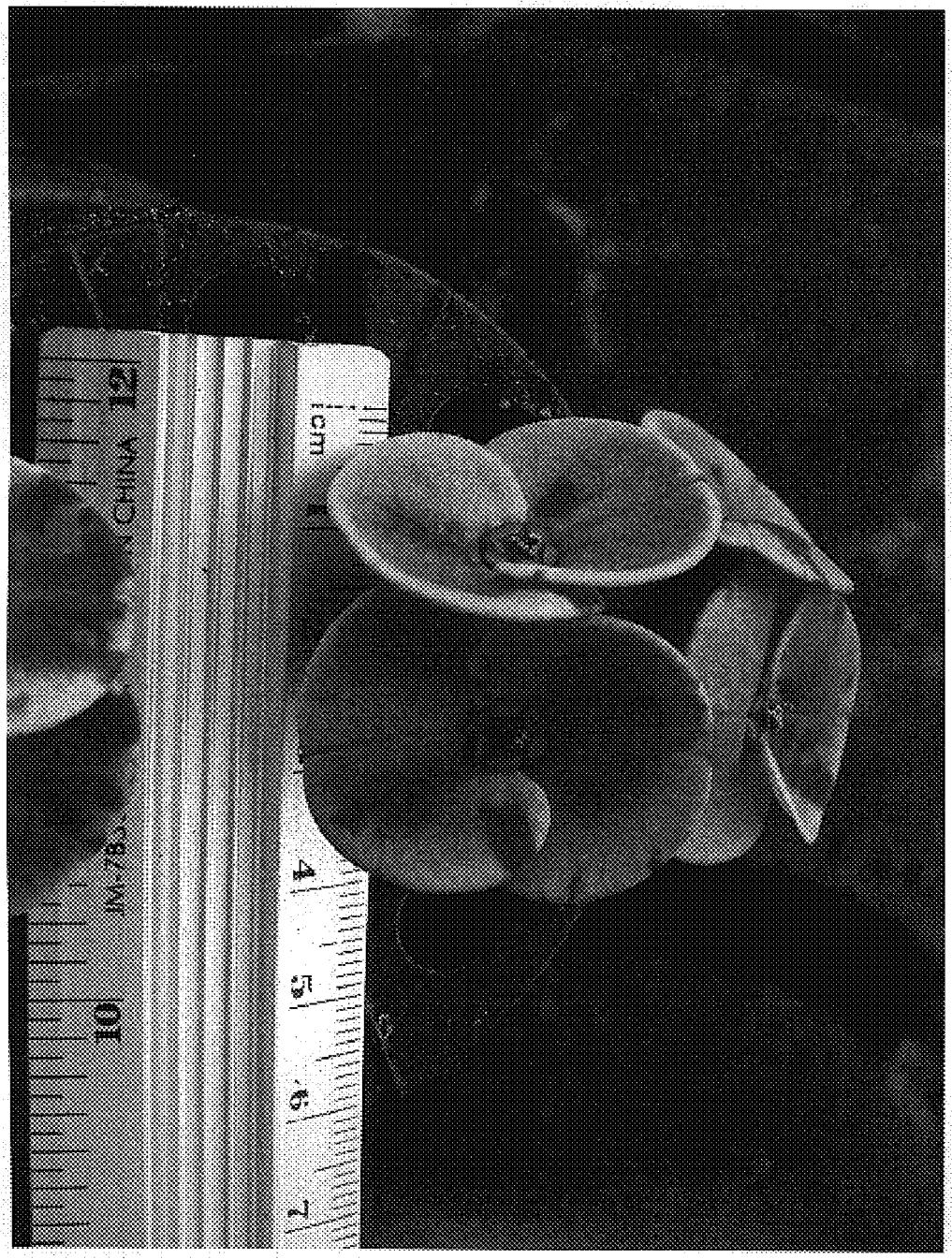
FIG. 14 shows a width of a typical inflorescence consisting of four cyathia, about 4 cm.
Figure 15:
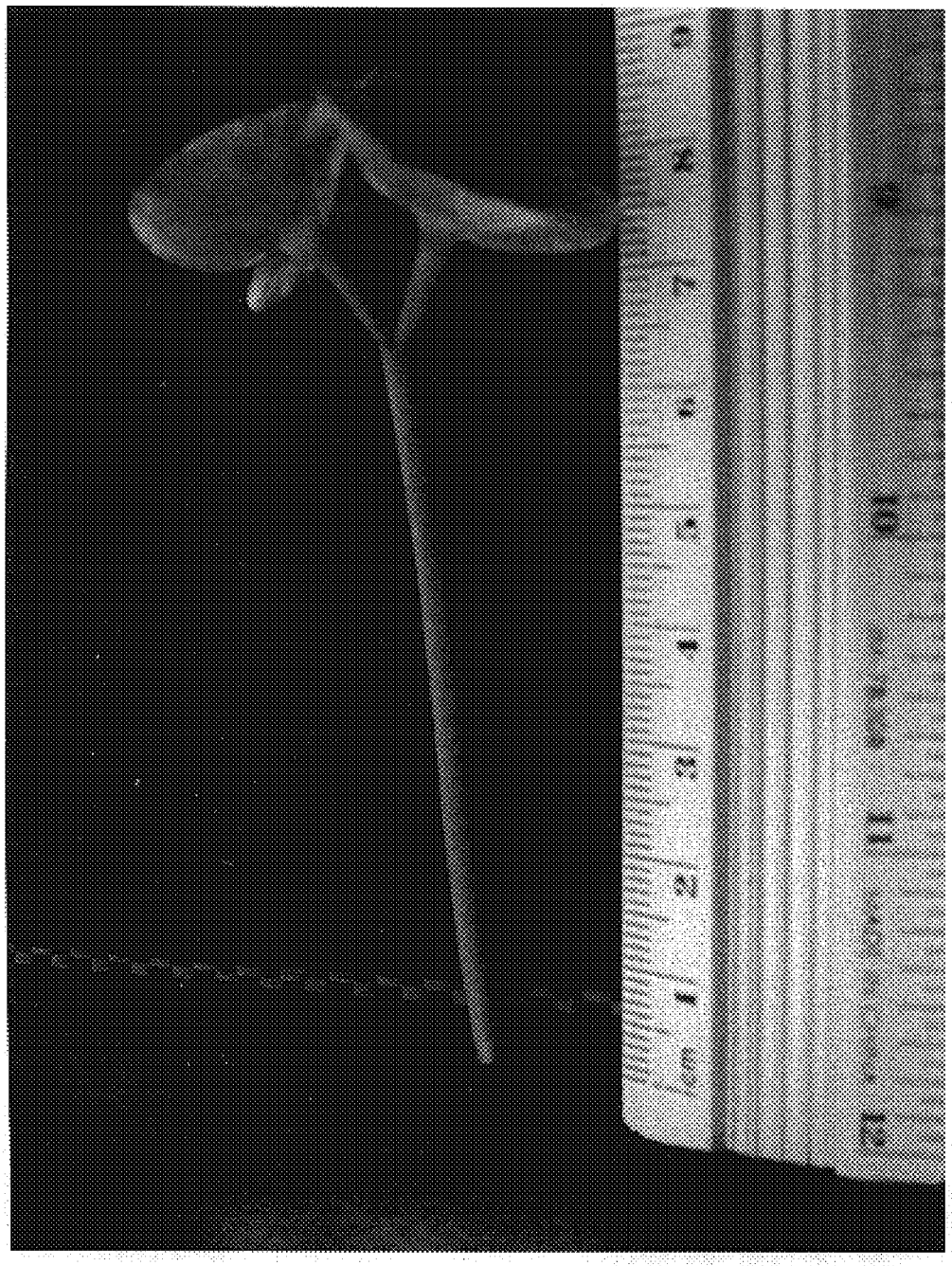
FIG. 15 shows a length of a typical peduncle, about 6.5 cm.
Figure 16:
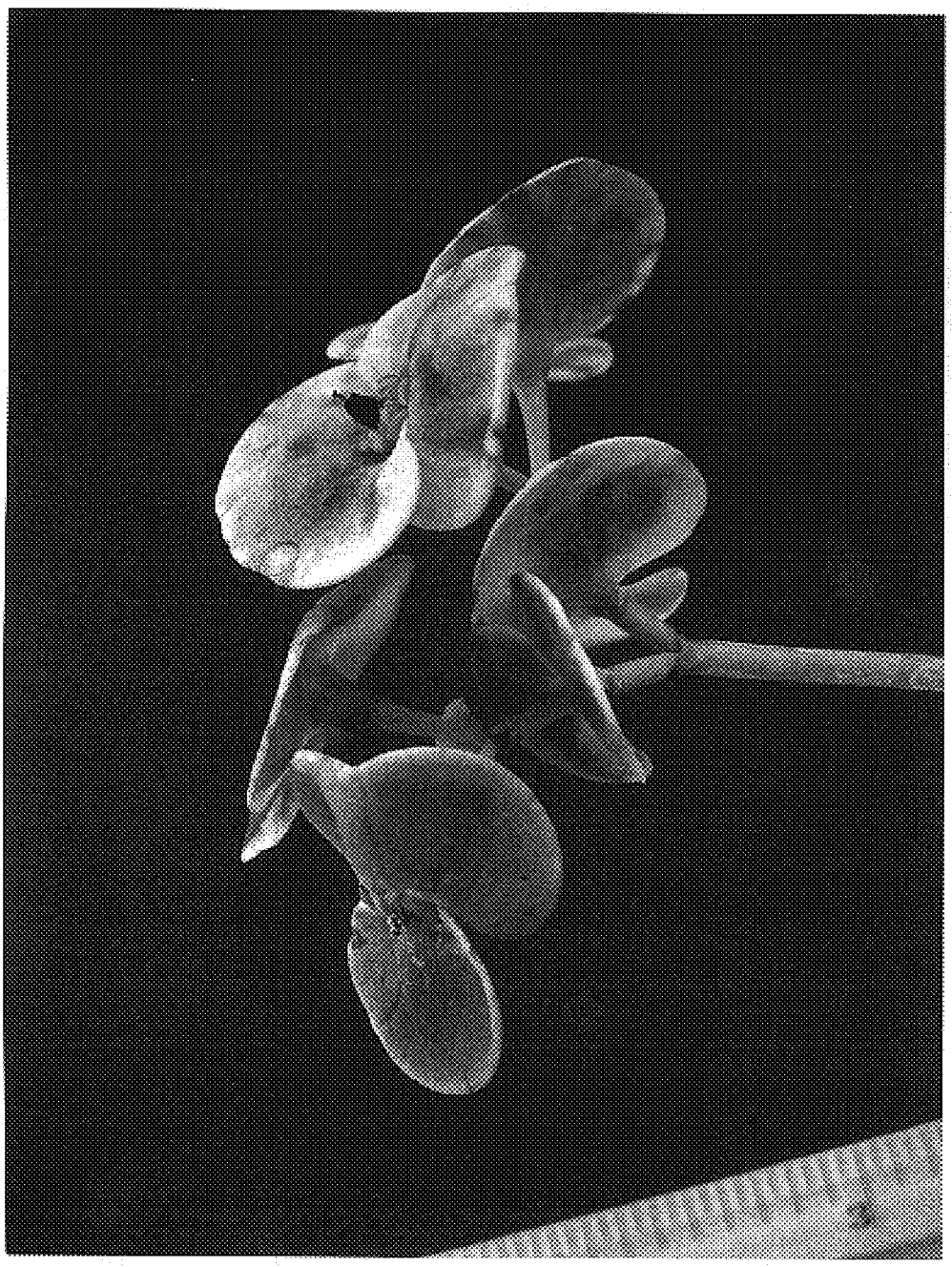
FIG. 16 shows older bracts as they lighten in color and extra cyathophylls* from which many additional cyathia emerge.

Note: *Euphoribia milii* "flowers" are actually specialized floral structures called cyathia (singular: cyathium). The large, colorful bracts are called cyathophylls, with the actual flower in the center. Five nectar glands surround the flower and may be colored in contrast to the cyathophylls.

DETAILED BOTANICAL DESCRIPTION

In the following description, color references are made to THE ROYAL HORTICULTURAL SOCIETY COLOUR CHART, 4th edition, where general terms of ordinary dictionary significance are used. Plants for this description were grown outdoors in full sunlight in southwest Florida. Plants were grown for about 8 months starting from cuttings taken in March. Cuttings were planted in potting soil in four inch pots with initial rooting in about three weeks, later transferred to six inch pots then finally to eight inch pots. Other pot sizes may be used depending upon the finished size of the plants desired. Plants are intended for outdoor use in temperate climates where plants will not freeze, or as container plants where they may be protected from freezing.

Botanical classification: *Euphorbia milii.* 'Katie's Crown'. Euphorbiaceae, Spurge family. Common English Name: Crown of Thorns.

Parentage: Female Parent: Unknown seedling plant of *Euphorbia milii.* Male Parent: Unknown seedling plant of *Euphorbia milii.*

Propagation:

*Type cutting.*—Terminal and stem cuttings taken from plants in the spring, as major growth period begins.

*Time to initiate roots.*—About three weeks in four inch pots, outdoors under partial shade in March in Naples, Fla.

*Root description.*—Fine and well branched.

PLANT DESCRIPTION

Form: Perennial plant with upright bushy habit. The new cultivar is compact and bushy, with multiple offshoots coming from single stems, where a fallen leaf had been attached to a stem a new branch will form. Multiple flower shoots, as many as 9 or 10, arising from single stems. Stems are generally round about 1.3 cm in diameter. Plants will grow about 30 cm in one summers growth period, holding leaves about 20 cm down the stem which adds to its bushy appearance. Single light violet blue thorns about 1 cm in length extend from stem.

Crop time: After rooting in April about 6–7 months are required to produce finished flowering plants in 20 cm pots in October.

Plant size: Soil level to top of plant plane after 7 months, about 30 cm, width about 30 cm.

Vigor: Very vigorous growth habit in south Florida from March through October. As soon as the fall season arrives in south Florida, around October, the plant puts its entire energy into blooming whereby its growth slows dramatically. For this reason, cuttings should be taken in the early summer when the plant is in its growth period.

Foliage description: Leaves simple, alternate, entire, elliptic to slightly obovate in shape. Length: 9 cm. Width: 3–4 cm: Apex. Obtuse. Base: Attenuate. Texture: Smooth, dull, slightly raised veining on undersides of leaves. Color: Young foliage, upper and lower surfaces yellow green (144A). Mature foliage, upper surface green (137A), lower surface slightly lighter green (138B). Venation: Pinnate, upper surface main vein green (137B), lower surface main vein (145B), lateral veins are the same color as the leaf surface. Main vein prominently raised on both upper and lower surface, lateral veins slightly raised.

Thorn description: Young thorns are Purplish (N77A) in appearance and rapidly turn to a light violet-blue color (92D) as thorns mature. Thorns are arranged randomly around the stem approximately 1 cm apart from each other.

Inflorescence description:

Inflorescence arrangement and shape: Floral arrangement composed of cymes, mostly in multiples of four extending from a single peduncle. Each cyathium is subtended by two overlapping hot pink floral bracts splotched with red referred to as cyathophylls. Immediately below many of the pairs of cyathia is an additional cyathophylls from which the pair of cyathia extends. Multiple peduncles, as many as nine or ten extending from a single stem.

Natural flowering season: Continuous throughout the fall, winter and spring in South Florida.

Inflorescence longevity on the plant: Six to eleven weeks. Cyathophylls sometimes lighten with age turning almost a cream color yellow (8D) with red (53B) splotches. Cyathophylls usually fall before they wither. Generally on those that hold long enough to change color there is a higher percentage of seed produced.

Inflorescence size: A typical cluster of four cyathia is about 4½ cm wide by about 5½ cm in length. Height, not including peduncle, about 2 cm.

Cyathophylls: Cordate and overlapping at base, rounded at apex, single cyathophylls 19 mm wide, 22 mm long. A single pair of cyathophylls is about 10 cm in diameter and is from 9 mm deep when immature, then gradually flattening to 2 mm deep as it matures.

Color of cyathophylls: Immature upper, background color red (50 C) with dark red splotches (53 B), immature lower; background light red (36 D) and splotching (52B) much lighter than upper side and with much less color definition. Mature upper, background slowly turning to a cream yellow (8D) with red splotches (53B). Mature lower, same color as upper but colors seem to flow together with less defined splotching.

Margins: Smooth, rounded with color matching cyathophylls. As cyathophylls mature the outer margins on both upper and lower surfaces lighten first, then gradually cyathophylls lightens inward to final mature color.

Cyathium: Small and slightly raised in center about 2 mm across, ovary superior, texture rough color (50 C) divided into three sections under which a maximum of three seeds, but mostly two are produced. Surrounded by five nectar glands.

Glands: 5 arranged end to end in an oval shape around cyathium, a single gland is oval shaped approximately 2 mm in length by 0.75 mm in width, shiny yellow orange (14 A) becoming dull with age.

Pistil and stigma: Stigma appears before cyathophylls are fully open. Slightly raised from ovary, but well below Stamen. Color, orange red (N 34 A).

Stamen: A light amount of bright yellow pollen is produced on a stamen that is about twice as tall as the Pistil. Anther color red (53 A).

Seeds: Usually produced in pairs of two, but sometimes three. Mature seeds are covered with a brown (200 A) pebbled skin. Seed inside skin is a yellow (161 A) color and almost round to reniform about 1 mm in diameter.

Peduncle: Strength: Strong. Length: 7 cm. Diameter: 2.5 mm. Color: Young stems, generally yellow green (144 B or C) but may sometimes be much darker to grayed orange (173 A). Mature stems, generally yellow green (144 B or C), but may sometimes be much darker to (152 A).

Pedicels: Length: 10 mm. Width: 2 mm Strength: Strong. Color. Generally matches peduncle in color.

Inflorescence buds: Strong, lanceolate shaped with obtuse tip. Color: Yellow green (144 A). Length closed, 7 mm. Width closed, 2 mm. Surface, smooth. As the buds mature the double overlapping sheath gradually opens and changes color and becomes the colorful cyathophylls with the flower in its center.

Weather tolerance: Plants of the new *Euphorbia milii* have exhibited good tolerance to drought, rain and wind. These plants have been grown outdoors for over two years in south Florida with no protection and with excellent results, however, as with most Crown of Thorns they should be protected from freezing.

Disease and pest tolerance: Plants of the new *Euphorbia milii* have exhibited excellent tolerance to pests and diseases. To this date, no known pests or diseases have been a problem with this plant.

I claim:

1. A new and distinct cultivar of *Euphorbia milii* plant named 'Katie's Crown', as illustrated and described herein.

* * * * *